United States Patent
De Vos

(10) Patent No.: US 8,203,008 B2
(45) Date of Patent: Jun. 19, 2012

(54) STABLE LACTIDE PARTICLES

(75) Inventor: Sicco De Vos, Arnhem (NL)

(73) Assignee: Purac Biochem B.V., Gorinchem (NL)

( * ) Notice: Subject to any disclaimer, the term of this patent is extended or adjusted under 35 U.S.C. 154(b) by 365 days.

(21) Appl. No.: 12/656,826

(22) Filed: Feb. 17, 2010

(65) Prior Publication Data
US 2010/0160650 A1 Jun. 24, 2010

Related U.S. Application Data

(60) Division of application No. 11/987,259, filed on Nov. 28, 2007, now abandoned, and a continuation-in-part of application No. 11/878,723, filed on Jul. 26, 2007, now abandoned.

(60) Provisional application No. 60/861,725, filed on Nov. 30, 2006.

(30) Foreign Application Priority Data

Nov. 28, 2006 (EP) .................................... 06124934
Jul. 26, 2007 (EP) .................................... 07113211

(51) Int. Cl.
*C07D 319/00* (2006.01)

(52) U.S. Cl. ...................................................... 549/274
(58) Field of Classification Search ................... 549/274
See application file for complete search history.

(56) References Cited

U.S. PATENT DOCUMENTS

| 1,995,970 A | 3/1935 | Dorough et al. |
| 5,053,485 A | 10/1991 | Nieuwenhuiset et al. |
| 5,264,592 A | 11/1993 | Fridman et al. |
| 5,646,238 A | 7/1997 | Ikeda et al. |
| 5,801,255 A | 9/1998 | Ohara et al. |
| 6,313,319 B1 * | 11/2001 | Ohara et al. .................. 549/274 |
| 6,875,839 B2 | 4/2005 | Gerking et al. |

FOREIGN PATENT DOCUMENTS

| EP | 1 310 517 A1 | 5/2003 |
| JP | A-63-152956 | 6/1988 |
| WO | WO 93/15127 A1 | 8/1993 |

OTHER PUBLICATIONS

Sarazin et al. "Controlled Preparation and Properties of Porous Poly( -lactide) Obtained from a Co-Continuous Blend of Two Biodegradable Polymers," Biomaterials, vol. 25, Issue 28, 2004, pp. 5965-5978.
Final Rejection of U.S. Appl. No. 11/987,256, mailed Nov. 19, 2009.
Non-Final Rejection of U.S. Appl. No. 11/987,256, mailed May 13, 2009.
Non-Final Rejection of U.S. Appl. No. 11/987,256, mailed May 12, 2010.

* cited by examiner

*Primary Examiner* — Nizal S Chandrakumar
(74) *Attorney, Agent, or Firm* — Oliff & Berridge, PLC

(57) ABSTRACT

The present invention is directed to stable lactide particles, more specifically lactide particles which are stable enough to be stored and transported at room temperature and have a quality high enough for use as starting material for polylactic acid. The lactide particles have a surface/volume ratio of the particle is lower than 3000. Preferably the lactide in the particle has an optical purity of at least 95%. The lactide particles are prepared by subjecting lactide to a shaping step comprising extrusion, pastillation, prilling, tabletting, or flaking.

16 Claims, 1 Drawing Sheet

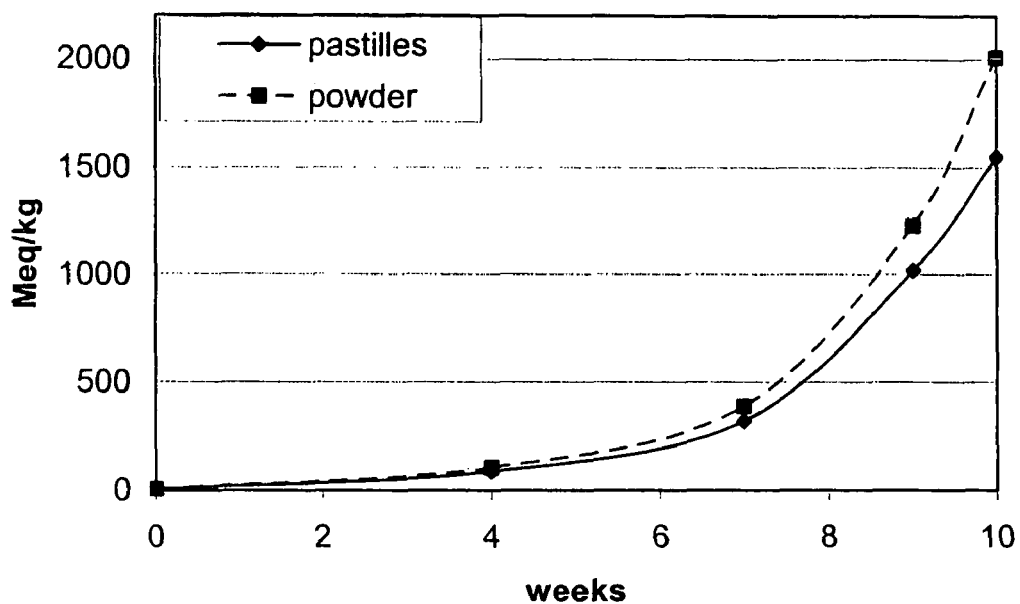
Figure 1: Free acid content after storage at 20 degrees Celcius in air
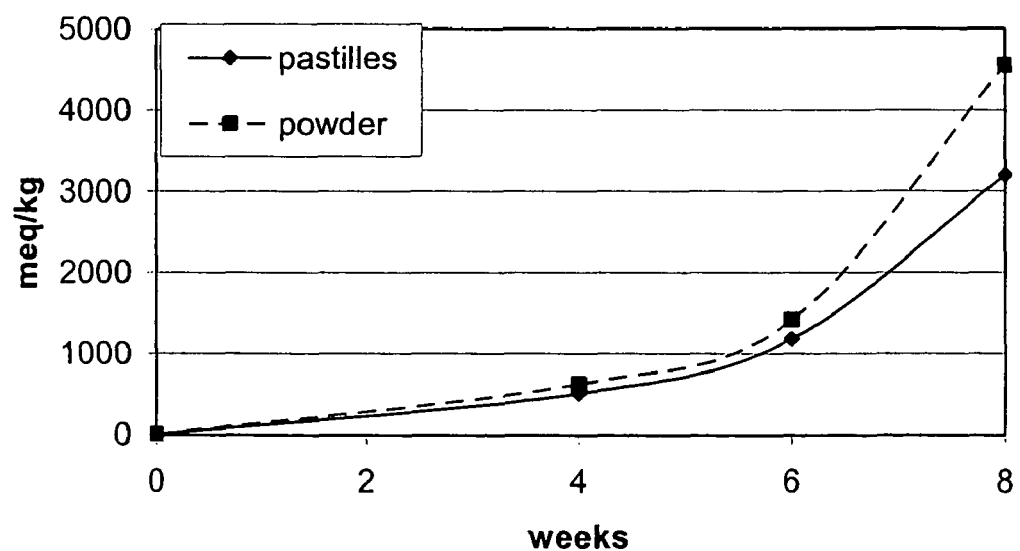
Figure 2: Free acid content after storage at 40 degrees Celcius in air

STABLE LACTIDE PARTICLES

This is a Division of application Ser. No. 11/987,259 filed Nov. 28, 2007, which is a non-provisional of Application No. 60/861,725 filed Nov. 30, 2006, and Continuation-in-part of application Ser. No. 11/878,723, filed Jul. 26, 2007. The disclosures of the prior applications are hereby incorporated by reference herein in their entirety.

The present invention relates to lactide particles, more specifically to lactide particles which are stable enough to be stored and transported at room temperature and which have a quality high enough for use as starting material for polylactic acid.

The continued depletion of landfill space and the problems associated with incineration of waste have led to the need for development of truly biodegradable polymers to be utilized as substitutes for non-biodegradable or partially biodegradable, petrochemical-based polymers in packaging, paper coating and other non-medical industry applications, hereinafter referred to as bulk applications. The use of lactic acid and lactide to manufacture a biodegradable polymer is well known in the medical industry. As disclosed by Nieuwenhuis et al. (U.S. Pat. No. 5,053,485), such polymers have been used for making biodegradable sutures, clamps, bone plates and biologically active controlled release devices. It will be appreciated that processes developed for the manufacture of polymers to be utilized in the medical industry have incorporated techniques that respond to the need for high purity and biocompatibility in the final polymer product. Furthermore, the processes were designed to produce small volumes of high dollar-value products, with less emphasis on manufacturing cost and yield.

It is known that lactic acid undergoes a condensation reaction to form polylactic acid upon dehydration. Dorough recognized and disclosed in U.S. Pat. No. 1,995,970, that the resulting polylactic acid is limited to a low molecular weight polymer of limited value, based on physical properties, due to a competing depolymerization reaction in which the cyclic dimer of lactic acid, lactide, is generated. As the polylactic acid chain lengthens, the polymerization reaction rate decelerates until it reaches the rate of the depolymerization reaction, which effectively, limits the molecular weight of the resulting polymers.

Therefore, in most publications, processes for the production for polylactic acid are described wherein from lactic acid first a prepolymer is prepared, said prepolymer is depolymerised by means of a catalyst to form crude lactide (i.e. the ring-closure reaction), said crude lactide is subsequently purified and lactide is used as starting material for the preparation of polylactic acid by ring-opening polymerization. For the purpose of this description the term polylactic acid and polylactide are used interchangeably. It is well known that lactic acid exists in two forms which are optical enantiomers, designated as D-lactic acid and L-lactic acid. Either D-lactic acid, L-lactic acid, or mixtures thereof may be polymerized to form an intermediate molecular weight polylactic acid which, after the ring-closure reaction, generates lactide as earlier disclosed. The lactide (sometimes also referred to as dilactide), or the cyclic dimer of lactic acid, may have one of three types of optical activity depending on whether it consists of two L-lactic acid molecules, two D-lactic acid molecules or an L-lactic acid molecule and a D-lactic acid molecule combined to form the dimer. These three dimers are designated L-lactide, D-lactide, and meso-lactide, respectively. In addition, a 50/50 mixture of L-lactide and D-lactide with a melting point of about 126° C. is often referred to in the literature as D,L-lactide. The optical activity of either lactic acid or lactide is known to alter under certain conditions, with a tendency toward equilibrium at optical inactivity, where equal amounts of the D and L enantiomers are present. Relative concentrations of D and L enantiomers in the starting materials, the presence of impurities or catalysts and time at varying temperatures, and pressures are known to affect the rate of such racemization. The optical purity of the lactic acid or the lactide is decisive for the stereochemistry of the polylactid acid obtained upon ring-opening polymerization of the lactide. With respect to polylactic acid, stereochemistry, and molecular weight are the key parameters for polymer quality.

When preparing polylactic acid for the medical industry often crystalline powdery lactide is used as the starting material. These crystals, which are commercially available for over 30 years now, are highly hygroscopic and are packed under inert atmosphere in damp- and air tight packages and stored in freezers (temperature below 12° C.). It will be clear that these precautions cannot be taken when polylactic acid is used for bulk applications because it would render the product too expensive.

In publications describing processes for the preparation of polylactic acid for bulk applications, the lactide formed and purified is directly fed in its molten, liquid form to a polymerization reactor to form polylactide. See for instance EP 0,623, 153 and U.S. Pat. No. 6,875,839. By the direct conversion of the lactide prepared to polylactic acid, the negative effects of the relative instability of lactide can be decreased by controlling the residence time of the lactide in the reactor. However, this process requires that the lactide production and polylactic acid production are combined. This makes the process rather inflexible and creates an entrance barrier for new polylactic acid producers, because it requires large investments in equipment. Secondly, as the quality of the lactide is decisive for the molecular weight and stereo-chemistry that can be obtained in the polylactic acid, and the ring-closure process and purification require strict control of the temperature, pressure and residence time, it is also the most delicate part of the polylactic acid production process. The risk of failure in this part of the process enlarges the entrance barrier even more. If new polylactic acid producers for bulk applications could simply be provided with stable high quality lactide, this burden would be taken from them and substitution of petrochemical-based polymers with polylactic acid could actually take place. It has been suggested to transport lactide in its melted form (melting point of D-lactide and L-lactide is 97° C.). Beside the fact that this type of transport is expensive, the transport and storage of melted lactide is also detrimental to the quality of the lactide because racemization, hydrolysis, and oxidation reactions are accelerated at these temperatures. The same problem occurs in the direct conversion process when the residence time of the lactide is not precisely controlled.

To this end the present invention is directed to stable lactide particles wherein the surface/volume ratio of the particle is lower than 3000 m$^{-1}$. We have found that lactide particles that fulfill this requirement are stable enough for storage and transport at room temperature and can readily be used as starting material for the production of lactic acid for bulk applications. This is surprising because the crystalline powdery lactides used for the medical industry are not stable enough over time.

FIG. 1 is a graph showing free acid content after storage at 20° C. in air, over time.

FIG. 2 is a graph showing free acid content after storage at 40° C. in air, over time.

As mentioned-above, the optical purity of the lactide is very important for the stereochemistry of the polylactic acid that is obtained. Therefore, it is preferred that the lactide present in the particles according to the invention contains more than 95% by weight D- or L-lactide, preferably more than 98.5% by weight D- or L-lactide, most preferably more than 99.5% D- or L-lactide by weight.

The lactide particles according to the invention can be prepared by subjecting lactide (for instance in the melted or crystalline powdery form) to a shaping process. Suitable shaping processes are extrusion, pastillation, prilling, flaking etcetera. The particles formed in the shaping process can be considered pellets, pastilles, granules and/or agglomerates. These terms are used throughout the description dependent from the term commonly used in the shaping process concerned.

By melted is meant that at least part of the lactide is at a temperature at or above the melting point of the lactide.

The apparatus used for the shaping process, or at least those parts that will be in contact with the lactide, preferably are prepared from corrosive-resistant material such as stainless steel. Further, to avoid water uptake of the lactide particles, the shaping process is preferably conducted under inert gas or dry atmosphere such as under nitrogen or dry air.

By means of extrusion through one or more dies cylindrical or rod-like particles can be obtained. When looking at the surface/volume ratio of the lactide particles, these cylindrical or rod-shaped particles are preferred. This shaping process is further preferred because processing equipment for the preparation of polylactide from lactide readily can handle particles of this shape because of the relatively uniform particle size and shape. The extruder is optionally cooled to avoid local overheating of the lactide. Any extruder conventionally used in the plastics, metal powder, food and ceramics industry such as screw extruders, such as single- and twin-screw extruders and radial screen extruders etcetera is suitable.

Suitable pastillation machines are for instance the disc pastillator, ex GMF® or a Rotoformer® ex Sandvik. Herein the lactide is melted and droplets are placed on a disk or belt with controlled temperature. We have found that by means of pastillation robust, uniformly shaped pellets can be made of lactide. Even though the surface/volume ratio of the resulting substantially hemi-spherical lactide particles is somewhat higher than for cylindrical or rod-shaped particles, hemi-spherical lactide particles are preferred because processing equipment for the preparation of polylactide from lactide readily can handle particles of this shape because of the relatively uniform particle size and shape. Moreover, with this shaping process virtually no dusting takes place and the resulting pastilles are hardly susceptible to abrasion during transport or any other mechanical handling. Compared to extruder-made particles, pastilles usually can easier be dosed in polylactic acid reactors especially when reactive extrusion polymerization is used. The term "relatively uniform" means that at least 90 percent by weight of the pastilles are within plus/minus 30 percent of the mean diameter. Preferably, at least 95 percent by weight of the particles are within plus/minus 10 percent of the mean diameter. The term "substantially hemi-spherical" means that the form of the particle is basically hemi-spherical, but can be flattened somewhat, i.e. the height of the particle is between 50 and 30% of its diameter.

When using flaking for the shaping process, optionally a sieving step is performed after the shaping to avoid dusting during transport and further processing to form polylactide.

With prilling lactide droplets fall in a liquid bath and thus spherical particles can be obtained. If water is used for the bath, extensive drying of the lactide particles is necessary.

Irrespective of the shape, particles with an average diameter of at least 3 millimeters are preferred, because then an optimum surface/volume ratio is ensured. More preferably the particles have an average diameter between 3 and 10 millimeters.

The water content of the lactide is an important factor for the stability of the lactide particles. Contamination by water vapor leads to ring-cleavage causing the lactide to convert to lactoyl lactic acid and lactic acid. It was found that if the water content is below 200 ppm the stability of the lactide particles when stored at room temperature in air-tight and vapor-tight packages is ensured for several months. Preferably, the water content is below 100 ppm because it further increases the stability of the lactide. The water content of the lactide can be measured by means of a Karl-Fisher titration as will be known by the artisan. Also the acid content of the lactide (either lactic acid or lactoyl lactic acid) is important for the stability and quality of the lactide. The presence of lactic acid and or lactoyl lactic acid in the feed to the final polymerization step will result in polymers of limited molecular weight. If the free acid content is below 50 milli-equivalents per Kg lactide (meq·Kg$^{-1}$) the stability of the lactide particles when stored at room temperature in air-tight and vapor-tight Packages is ensured for several months. Preferably, the acid content is below 20 meq·Kg$^{-1}$ because it further increases the stability of the lactide. Most preferably the acid content is between 0 and 10 meq·Kg$^{-1}$. The acid content can be measured by means of titration using for instance sodium methanoate or potassium methanoate, as will be clear for the artisan.

The lactide used as starting material for the shaping process may have been prepared by any conventional lactide process such as water removal from a lactic acid solution or condensation reaction of lactate esters, followed by a ring-closure reaction in a lactide reactor with the help of a catalyst. Optionally the crude lactide is further purified by for instance distillation and/or crystallization prior to the shaping process.

The lactide reactor can be of any suitable type that is designed for heat sensitive materials. A reactor that can maintain a uniform film thickness, such as a falling film or agitated thin-film evaporator is most preferred, because film formation increases the rate of mass transfer. When the rate of mass transfer is increased, lactide can quickly form and vaporize, and as lactide vaporizes, more lactide is produced as dictated by the polylactic acid/lactide equilibrium reaction. Optionally these lactide reactors are operated under reduced pressure such as between about 1 mmHg and 100 mmHg. The temperature of the lactide formation is kept between 150° C. and 250° C. Many suitable catalysts are known, such as metal oxides, metal halides, metal dusts, and organic metal compounds derived from carboxylic acids or the like. Normally a tin(II) oxide or tin(Oct)$_2$ catalyst is used for lactide formation.

Stabilizers may also be added to the lactide reactor in order to facilitate lactide formation and discourage degenerative lactic acid and lactide reactions. Stabilizers, such as antioxidants, can be used to reduce the number of degradation reactions that occur during the process of polylactic acid and lactide production. Stabilizers may also reduce the rate of lactide formation during this process. Therefore, efficient production of lactide requires proper reactor design for minimal thermal severity and a proper balance between the catalyst and any use of process stabilizers.

A variety of stabilizers may be used. The stabilizing agent may include primary antioxidants and/or secondary antioxidants. Primary antioxidants are those which inhibit free radical propagation reactions, such as alkylidene bisphenols, alkyl phenols, aromatic amines, aromatic nitro and nitroso compounds, and quinones. To prevent formation of free radicals secondary (or preventive) antioxidants break down hydroperoxides. Some examples of secondary antioxidants include: phosphites, organic sulfides, thioethers, dithiocarbamates, and dithiophosphates. Antioxidants, when added to the lactide reactor can reduce the extent of racemization during lactide production. This reduction indicates that the addition of antioxidants is an additional means to control optical purity. Antioxidants include such compounds as trialkyl phosphites, mixed alkyl/aryl phosphites, alkylated aryl phosphites, sterically hindered aryl phosphites, aliphatic spirocyclic phosphites, sterically hindered phenyl spirocyclic, sterically hindered bisphosphonates, hydroxyphenyl propionates, hydroxy benzyls, alkylidene bisphenols, alkyl phenols, aromatic amines, thioethers, hindered amines, hydroquinones, and mixtures thereof. Preferably, phosphite-containing compounds, hindered phenolic compounds, or other phenolic compounds are used as process stabilizing antioxidants. Most preferably, phosphite-containing compounds are used. The amount of process stabilizer used can vary depending upon the optical purity desired of the resulting lactide, the amount and type of catalyst used, and the conditions inside of the lactide reactor. Normally amounts varying form 0.01 to 0.3 wt. % process stabilizer can be used.

It is also possible to add these process stabilizers to the lactide at a later stage, such as for instance prior to the shaping and/or after the shaping step. If the stabilizers are added to the lactide after shaping, the stabilizers may be sprayed or coated onto the lactide particles.

Its is of course desired to have as little as possible material such as process stabilizers present in the lactide particles other than lactide. Therefore, the lactide particle usually comprises more than 95% by weight lactide, preferably more than 98.5% by weight lactide, most preferably more than 99.5% by weight.

Depending on the lactide preparation and/or purification method and the type of shaping process, the shaping process can either be combined with the preparation and or purification, or not. For instance, if the lactide is obtained form distillation, it makes sense to directly couple a pastillation machine to the distillation column because the lactide is already in its melted form. If the final purification step of the lactide comprises crystallization, the use of an extruder is more opportune. Said extrusion can also take place at a later point in time.

We have found that the presence of the above-mentioned process stabilizers also increases the stability of the lactide particles during storage.

The invention is further illustrated by means of the following non-limiting examples

EXAMPLE 1

Pastillation of L-Lactide Using Lab-Scale Disc Pastillator

Fresh L-lactide ex. Purac® (<1 meq/Kg free lactic acid) was molten using a microwave and subsequently poured into a double-walled metal container that was continuously heated by means of a hot air current. The lactide was thus kept in the molten state, and covered with a metal plunger. At the bottom of the heated container, a nozzle with a cylindrical die (D=1 mm) was mounted. A slight pressure was applied to the lactide melt resulting in droplets falling onto a RVS disc that was mounted 6-7 mm below the nozzle. The RVS disc (D=400 mm) was slowly rotating (1-2 rpm), did not have active cooling and had a temperature of 15-20° C. (RT). The clear lactide melt discharged from the nozzle solidified and crystallized on the RVS disc producing white pastilles. The droplet falling rate and the disc rotation speed were matched in order to get circular arrays of pastilles on the disc. As soon as a circular array of pastilles was full, the position of the nozzle over the disc was adapted to start a new array, thus producing a cooling disc ultimately covered with concentric arrays of pastilles. Pastilles did not stick to the metal disc and could be collected easily. Solidified lactide pastilles of uniform dimensions could thus be produced (Average particle diameter 5.5-6 mm with a thickness of between 1.6-1.8 mm).

EXAMPLE 2

Cylindrical L-Lactide Pellets Produced by Extrusion

Fresh L-lactide ex. Purac® (<1 meq/Kg free lactic acid) was extruded through a single capillary die of a Prism Pharmalab 16 Series co-rotating twin-screw extruder of Thermo Fisher Scientific Corporation. The screw diameter was 16 mm and the processing length L/D was 40. The temperatures (° C.) of the electrically heated zones (#1-11) of the extruder barrel were:

|   | die |   |   | mixing section |   |   | mixing section |   |   |   | feed |
|---|---|---|---|---|---|---|---|---|---|---|---|
| # | 11 | 10 | 9 | 8 | 7 | 6 | 5 | 4 | 3 | 2 | 1 |
| ° C. | 92 | 95 | 90 | 85 | 80 | 75 | 70 | 70 | 60 | 50 | 10 |

The extruder was operated with a screw speed of 150 rpm and L-lactide powder was metered in water-cooled zone 1 at a solids rate of 1.8-2.4 Kg/h by means of a volumetric feeder. The temperature of the white paste discharged from the die was 88-92° C. The resulting strands broke spontaneously when they fell down some 20-40 cm upon discharge from the extruder onto an RVS tray. As a result, cylindrical pellets with a randomly distributed length of several millimeters are obtained (the particle diameter was about 3 mm while the length varied from 5 to 15 mm).

The white lactide pellets initially exhibited a free lactic acid content of 4 meq/Kg.

COMPARATIVE EXAMPLE 3

The stability of powdery lactide particles was tested. The surface/volume ratio of powdery lactide is given in the TABLE below:

| Shape | Average particle diameter (mm) | Surface/volume ratio ($m^2/m^3$) |
|---|---|---|
| Powder (spherical) | 0.001 | 6,000,000 |
|  | 0.005 | 1,200,000 |
|  | 0.01 | 600,000 |
|  | 0.02 | 300,000 |
|  | 0.1 | 60,000 |
|  | 0.2 | 30,000 |
|  | 0.5 | 12,000 |

The stability of powdery material having a diameter of about 1 mm (surface/volume ratio of 6000 $m^{-1}$) was measured after storage for 1 year in air-tight and vapor-tight bags (comprising a polyethylene inner bag and an aluminum outer bag) with a hole in it. The initial free acid content was 0.080 meq/Kg. After 1 year at 4° C. the free acid content was increased to 0.09 meq/Kg and after 1 year at 25° C. the free acid content was increased to 1131 meq/Kg. This means shows that powdery material is not stable enough for storage at room temperature for several months.

COMPARATIVE EXAMPLE 4

The stability of powdery material having a diameter of about 1 mm was measured after storage for 1 year in a single polyethylene bag (vapor-tight but not air-tight). The initial free acid content was 0.09 meq/Kg. After 6 months at 25° C. the free acid content was increased to 405 meq/Kg, and thus not suitable anymore as a starting material for the preparation of polylactid acid.

EXAMPLE 5

In the TABLE below the surface/volume ratio is given for cylindrical and hemi-spherical shaped lactide particles.

| Shape | | Surface/volume ratio ($m^2/m^3$) |
|---|---|---|
| | Average particle length × diameter (mm × mm) | |
| Cylindrical | 2 × 1.5 | 2000 |
| | 3 × 1.5 | 1333.4 |
| | 4 × 1.5 | 1000 |
| | 5 × 1.5 | 800 |
| | 6 × 1.5 | 666.7 |
| | 7 × 1.5 | 571.4 |
| | 8 × 1.5 | 500 |
| | 9 × 1.5 | 444.4 |
| | 10 × 1.5 | 400 |
| | Average particle diameter (mm) | |
| Hemi-spherical | 2 | 4500 |
| | 3 | 3000 |
| | 4 | 2250 |
| | 5 | 1800 |
| | 6 | 1500 |
| | 7 | 1286 |
| | 8 | 1125 |
| | 9 | 1000 |
| | 10 | 900 |

The invention claimed is:

1. Process for the preparation of lactide particles, the process comprising:
    shaping lactide to form the lactide particles having a surface/volume ratio lower than 3000 $m^{-1}$,
    wherein the shaping comprises extrusion, pastillation, compression, or flaking,
    wherein the lactide particles are stable lactide particles having an initial free acid content of at most 5 milli-equivalents per kilogram lactide (meq/kg) at 20° C. in air, and a free acid content after 10 weeks of storage below 2000 meq/kg,
    wherein the stable lactide particles have a water content below 200 ppm, and
    wherein the stable lactide particles have a free lactic acid content below 50 meq/kg.

2. Process according to claim 1, wherein the lactide is extruded or compressed to form cylindrical, cubical or rod-shaped particles.

3. Process according to claim 1, wherein the lactide is a lactide melt that is pastillated to form substantially hemi-spherical particles.

4. Process according to claim 1, wherein the shaping comprises flaking process, and the flakes are sieved.

5. Process according to claim 1, wherein the process is carried out under an inert or dry atmosphere.

6. Process according to claim 1, wherein the process is carried out in an apparatus, and parts of the apparatus that are in contact with the lactide are prepared from a corrosion-resistant material.

7. Process according to claim 1, wherein the process is carried out in such a manner that the stable lactide particles with a diameter of at least 3 mm are obtained.

8. Process according to claim 1, wherein the stable lactide particles comprise more than 95% by weight lactide.

9. Process according to claim 1, wherein the lactide in the stable lactide particles contains more than 95% by weight D-lactide.

10. Process according to claim 9, wherein the lactide in the stable lactide particles contains more than 99.5% by weight D-lactide.

11. Process according to claim 1, wherein the lactide in the stable lactide particles contains more than 95% by weight L-lactide.

12. Process according to claim 11, wherein the lactide in the stable lactide particles contains more than 99.5% by weight L-lactide.

13. Process according to claim 1, wherein the stable lactide particles have a water content below 100 ppm.

14. Process according to claim 13, wherein the stable lactide particles have a water content below 50 ppm.

15. Process according to claim 1, wherein the stable lactide particles have a free lactic acid content below 20 meq/kg.

16. Process according to claim 15, wherein the stable lactide particles have a free lactic acid content between 0 and 10 meq/kg.

* * * * *